United States Patent
Ruch et al.

(10) Patent No.: US 9,582,997 B2
(45) Date of Patent: Feb. 28, 2017

(54) METHOD AND DEVICE FOR REMOTE CONTROL OF MEDICAL APPARATUS USING A REMOTE CONTROL DEVICE

(71) Applicant: MAQUET GMBH, Rastatt (DE)

(72) Inventors: Juergen Ruch, Offenburg (DE); Andreas Hirth, Rastatt (DE)

(73) Assignee: MAQUET GMBH, Rastatt (DE)

( * ) Notice: Subject to any disclaimer, the term of this patent is extended or adjusted under 35 U.S.C. 154(b) by 0 days.

(21) Appl. No.: 14/944,416

(22) Filed: Nov. 18, 2015

(65) Prior Publication Data

US 2016/0328958 A1 Nov. 10, 2016

Related U.S. Application Data

(63) Continuation-in-part of application No. PCT/EP2014/060330, filed on May 20, 2014.

(30) Foreign Application Priority Data

Jun. 6, 2013 (DE) .......................... 10 2013 105 822

(51) Int. Cl.
*H04B 10/114* (2013.01)
*G08C 23/04* (2006.01)
(Continued)

(52) U.S. Cl.
CPC ........... *G08C 23/04* (2013.01); *G06F 19/3418* (2013.01); *G08C 17/02* (2013.01);
(Continued)

(58) Field of Classification Search
CPC ............. H04B 10/1143; G06F 19/3418; G06F 19/3406; G08C 17/02; G08C 23/04; G08C 2201/20
(Continued)

(56) References Cited

U.S. PATENT DOCUMENTS 9,168,006 B2 * 10/2015 Georgiev ............... G08C 17/02
9,312,949 B1 * 4/2016 Templeton ............... H04B 7/26
(Continued)

FOREIGN PATENT DOCUMENTS

DE 102007060808 A1 3/2009
EP 1312332 A1 5/2003
(Continued)

OTHER PUBLICATIONS

International Search Report dated Oct. 8, 2014, issued in PCT/EP2014/060330 (with English translation).

*Primary Examiner* — Dalzid Singh

(57) ABSTRACT

An operating table control apparatus is disclosed. The operating table control apparatus has a remote control device, a first transmitting-receiving device that is mountable to the remote control device, and a second transmitting-receiving device that is mountable to a first operating table. The first transmitting-receiving device is configured to transmit a request command to the second transmitting-receiving device. After receiving the request command from the first transmitting-receiving device, the second transmitting-receiving device is configured to transmit a device address of the first operating table to the first transmitting-receiving device. The first transmitting-receiving device is configured to adopt the device address received from the second transmitting-receiving device, establishing a paired operating state between the first transmitting-receiving device and the second transmitting-receiving device. The first transmitting-receiving device is configured to transmit both a control command and the device address to the second transmitting-receiving device.

20 Claims, 3 Drawing Sheets

(51) Int. Cl.
   *G08C 17/02*     (2006.01)
   *G06F 19/00*     (2011.01)
(52) U.S. Cl.
   CPC ...... *H04B 10/1143* (2013.01); *G06F 19/3406* (2013.01); *G08C 2201/20* (2013.01)
(58) Field of Classification Search
   USPC .......................................................... 398/107
   See application file for complete search history.

(56) References Cited

U.S. PATENT DOCUMENTS

| | | |
|---|---|---|
| 2008/0312512 A1 | 12/2008 | Brukalo et al. |
| 2009/0063187 A1 | 3/2009 | Johnson |
| 2009/0126115 A1 | 5/2009 | Doering et al. |
| 2012/0185267 A1 | 7/2012 | Kamen |
| 2013/0057778 A1 | 3/2013 | Hale |
| 2013/0096701 A1* | 4/2013 | Suorajaervi ............ A61G 13/02 700/83 |

FOREIGN PATENT DOCUMENTS

| | | |
|---|---|---|
| EP | 1486099 B1 | 12/2004 |
| EP | 1785965 A2 | 5/2007 |
| EP | 2209413 B1 | 8/2011 |
| WO | WO 2007113884 A1 | 10/2007 |

* cited by examiner

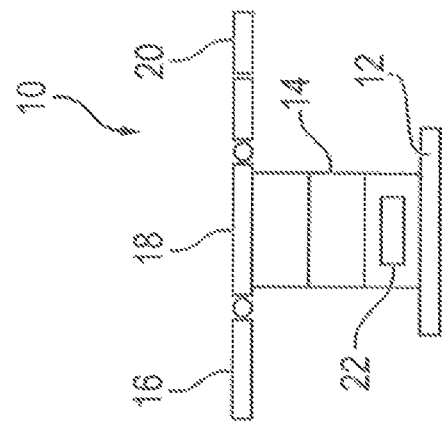
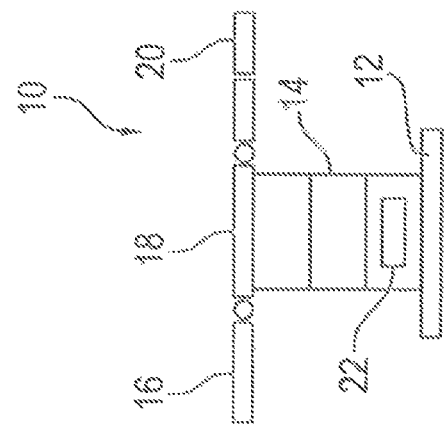
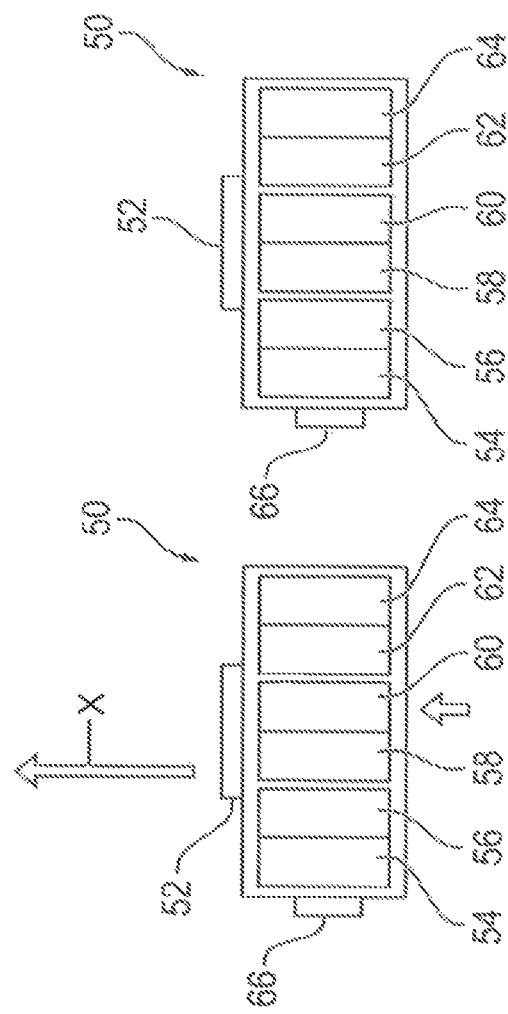
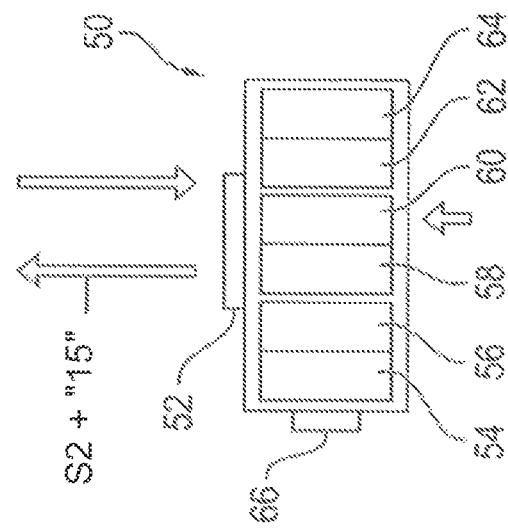

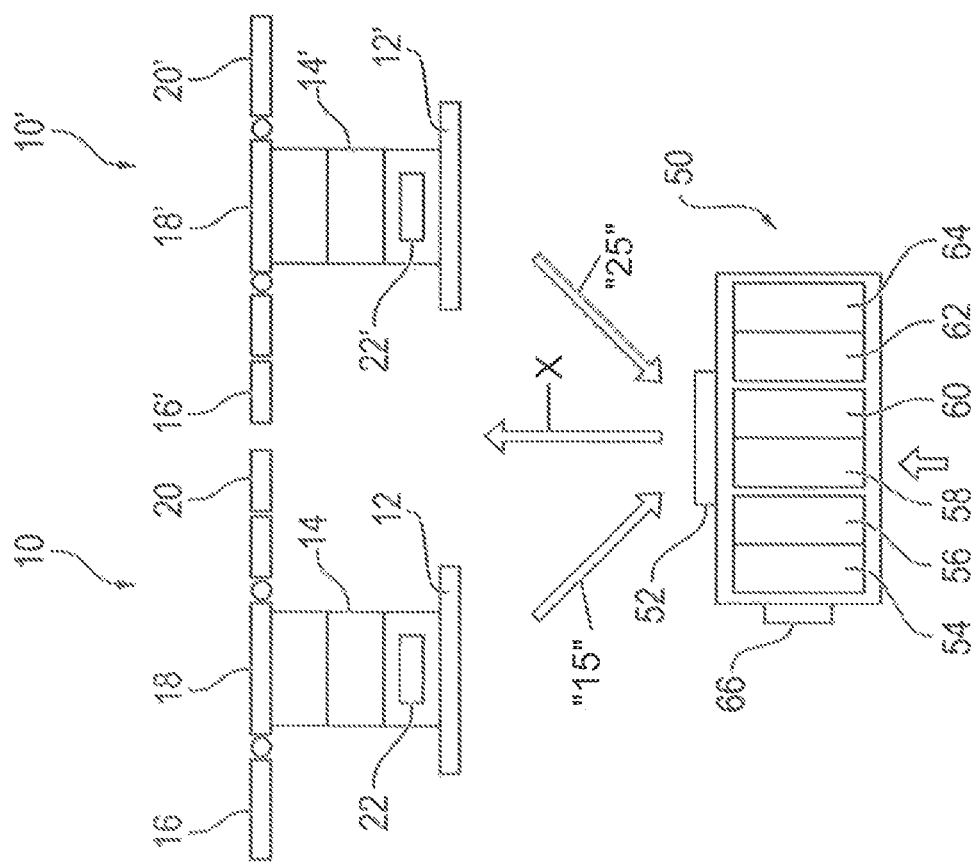

METHOD AND DEVICE FOR REMOTE CONTROL OF MEDICAL APPARATUS USING A REMOTE CONTROL DEVICE

CROSS REFERENCE TO RELATED APPLICATIONS

The present application is a continuation-in-part filed under 35 U.S.C. §111(a), and claims the benefit under 35 U.S.C. §§365(c) and 371 of PCT International Application No. PCT/EP2014/060330, filed May 20, 2014, and which designates the United States of America, and German Patent Application No. 10 2013 105 822.1, filed Jun. 6, 2013. The disclosures of these applications are herein incorporated by reference in their entirety.

TECHNICAL FIELD

The present disclosure relates to a method of remotely controlling a medical apparatus using a control device such as a remote control device. For example, a paired operating state may be established between a first infrared transmitting-receiving unit of a remote control device and a second infrared transmitting-receiving unit of a respective medical apparatus, a remote control address transmitted by the first infrared transmitting-receiving unit being, e.g., a device address preset for the second infrared transmitting-receiving unit, in said paired operating state. A presence of the paired operating state may be verified; and the medical apparatus may be controlled in response to a control command sent from the first infrared transmitting-receiving unit to the second infrared transmitting-receiving unit upon operation of the remote control device when the paired operating state is present.

BACKGROUND

In medical technology, remote control devices using infrared radiation are employed for controlling medical apparatuses, such as operating tables by remote control. For this purpose, the remote control devices and the medical apparatus to be controlled are provided with infrared transmitting-receiving units which communicate with each other via infrared signals.

Before it is possible to remotely control the medical apparatus via the remote control device, verification is made as to whether a remote control device should be paired with a given medical apparatus. If so, the medical apparatus can be remotely controlled via control commands sent by the remote control device to the medical apparatus upon corresponding operation of the remote control device.

Typically, a pairing once established is maintained until the remote control device is paired with another apparatus, e.g., until the remote control address is manually switched to the device address of said other apparatus. Switching of the remote control device is unpractical, in particular if such switching must be performed frequently. This applies, for example, if a plurality of operating tables is to be selectively actuated for pre- or postoperative support transfer using only one remote control device, such as a pedal or a hand-held device.

SUMMARY OF THE DISCLOSURE

In at least some exemplary embodiments of the present disclosure, in order to remotely control only one apparatus among a plurality of medical apparatuses using only one single remote control device, a paired operating state may be established between an infrared transmitting-receiving unit of the remote control device and an infrared transmitting-receiving unit of the medical apparatus to be controlled, wherein an infrared remote-control address sent by the remote control device to the medical apparatus may be substantially equal to an infrared device address which has been individually preset for the respective medical apparatus. For example, the paired operating state may be established by setting the remote control address to the same address as the device address preset for the medical apparatus to be controlled via a rotary encoder switch provided on the remote control device. As an alternative, pairing between the remote control device and the medical apparatus can be established via a computer based menu.

It is the object of the present disclosure to further develop a method of remotely controlling a medical apparatus such that a paired operating state between a remote control device and the medical apparatus to be controlled can be established in a simple and secure manner.

In the present disclosure, a paired operating state may be established by a request command being sent from a first infrared transmitting-receiving unit to a second infrared transmitting-receiving unit upon start-up of a remote control device, the preset device address being sent from the second infrared transmitting-receiving unit to the first infrared transmitting-receiving unit upon receipt of the request command, and the device address received by the first infrared transmitting-receiving unit being adopted as a remote control address.

Accordingly, the method according the present disclosure may provide automatic pairing between infrared transmitting-receiving units of a remote control device and an apparatus to be controlled. Upon start-up of the remote control device, the device may request the infrared device address of the apparatus addressed thereby. The remote control device may subsequently adopt this device address as a remote control address and may use the device address for further communication with the apparatus addressed. Manual switching of the remote control address to the device address fixedly preset for the apparatus to be controlled may, for example, thus be omitted.

The present disclosure may provide for sending the request command to the addressed medical apparatus upon start-up of the remote control device. Therein, "start-up" for example may involve a first operation of the remote control device by which the apparatus is to be controlled in order to, for example, adjust the patient support of the operating table. "Start-up" can, however, also involve turning on the remote control device, e.g., the beginning of energy supply, if a turn-on function of this type is provided in the remote control device. Likewise, "start-up" may involve the first operation of the remote control device after a predetermined period of time has elapsed. This period of time can be set in accordance with the apparatus to be controlled and the processes to be carried out, for example such that it determines a time after which it is to be expected that another apparatus among the group of apparatus is to be addressed with the remote control device.

For example, as any apparatus of a group of apparatuses in use can be addressed with the remote control device due to the automatic pairing according to the present disclosure, the remote control device can simply be replaced by another remote control device currently used for the same group of apparatuses, e.g. after loss or upon malfunction. In this way, for example, an operation of the group of apparatuses may be suitably maintained.

A presence of the paired operating state may be verified by the device address, after it has been adopted by the first infrared transmitting-receiving unit as a remote control address, being cyclically transmitted by the second infrared transmitting-receiving unit, and by the remote control device verifying whether the first infrared transmitting-receiving unit cyclically receives the device address. Thus, in at least some exemplary embodiments of the present disclosure, the device address preset for the addressed apparatus may be adopted upon start-up of a remote control device, and it may be subsequently cyclically verified whether or not the pairing once established is being maintained.

Also, in at least some exemplary embodiments of the present disclosure, a presence of the paired operating state can also be verified by the remote control detecting whether or not the first infrared transmitting-receiving unit receives any other device address besides the adopted one. Should the remote control device, for example, receive two different device addresses at the same time, it may be possible to cancel pairing of the remote control device with the apparatus initially addressed, and thus substantially prevent remote control of said apparatus. This may allow for secure apparatus control by the remote control device.

A presence of the paired operating state may also be verified by detecting a movement of the remote control device. If, for example, the remote control device is a pedal, this pedal can have a motion sensor which detects lifting of the pedal from the floor and outputs a corresponding signal such that the pairing between a remote control device and an addressed apparatus which was initially established is cancelled. This function may allow for reliable and secure control of the apparatus.

The device address adopted by the first infrared transmitting-receiving unit may be stored in the remote control device. Upon a subsequent start-up of the remote control device, the device address stored based on the previous start-up can be transmitted by the first infrared transmitting-receiving unit to the second infrared transmitting-receiving unit as the remote control address. If the remote control device is, for example, a hand-held device provided with operator buttons, the remote control device may be initially started with the remote control address that was last adopted. This may allow for a relatively short response time (e.g., if the same apparatus is still to be controlled with the remote control device).

For example, in the case that the remote control address sent to the second infrared transmitting-sending unit upon a subsequent start-up of the remote control device is different from the device address preset for the second infrared transmitting-sending unit, a request may be sent as output by the remote control device for the user to confirm the device address. For example, in the case of confirmation, the device address may adopted by the first infrared transmitting-receiving unit as a remote control address. For example, if it is determined that the currently addressed apparatus responds with a device address different from that used before, the user may be requested to first confirm the newly recognized device address if he/she intends to control the apparatus to which this new device address is assigned. Thus, for example, remote control of the apparatus may be optimized and made more reliable.

For example, in the case of a paired operating state, the control command may be sent together with the remote control address with each operation of the remote control device (e.g., from the first infrared transmitting-receiving unit to the second infrared transmitting-receiving unit). Thus, during each instance of operation it is possible to verify for the addressed apparatus whether the remote control address received is substantially equal to the preset device address. Thus, for each operation of the remote control device, it may be verified whether the operating device and the apparatus are still operatively paired with each other.

According to a further aspect of the present disclosure, a device may be provided that may be adapted to perform the method disclosed herein.

BRIEF DESCRIPTION OF THE DRAWINGS

Exemplary embodiments of the present disclosure are explained in more detail with reference to the following Figures.

FIG. 4 is a schematic illustration showing the first exemplary embodiment when sending a further control command to the operating table;

FIG. 5 is a schematic illustration showing the first exemplary embodiment when sending a further control command in a non-paired operating state;

FIG. 6 is a schematic illustration showing a second exemplary embodiment prior to start-up of the pedal switch;

FIG. 7 is a schematic illustration showing the second exemplary embodiment when receiving device addresses of two operating tables; and FIG. 8 is a schematic illustration showing the second exemplary embodiment in a non-paired operating state.

In FIGS. 1 to 5, a first exemplary embodiment of the method according to the present disclosure is illustrated. In a first embodiment, an operating table 10 may be remotely controlled by a remote control device. The remote control device may be any suitable device for receiving input from a user for use in remotely controlling an operating table system such as, for example, a hand-held remote control (e.g., wireless or wired control), a monitor display such as a touch-screen monitor, a personal computer, a voice-activated input device, an integrated operating room control system, or a pedal system or other mechanical device for receiving input. The remote control device may be, for example, a pedal switch 50.

Figure 1:
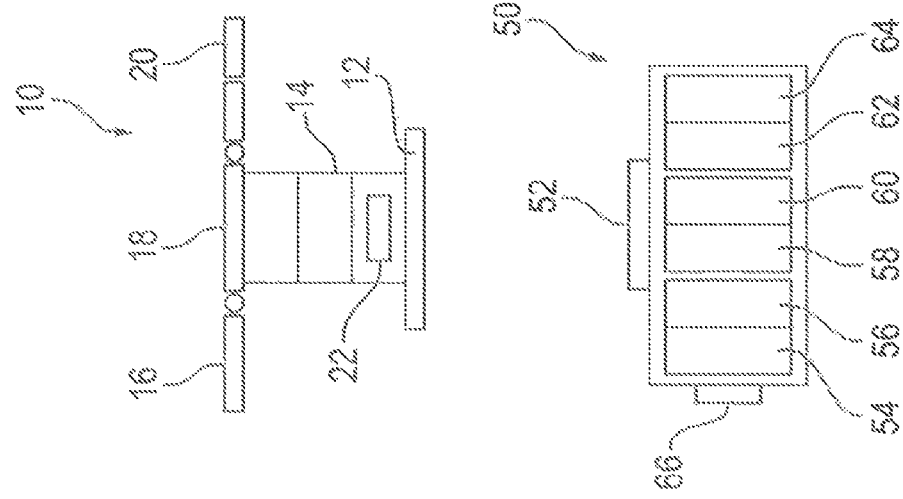
FIG. 1 is a schematic illustration showing a pedal switch and an operating table in a first exemplary embodiment prior to start-up of the pedal switch.

The operating table 10 may have a base 12 and a table column 14 mounted thereon. The table column 14 may be vertically adjustable. A patient support including a plurality of segments 16, 18, and 20 which may be adjustable with respect to each other, may be attached to an upper end of the table column 14. For adjustment of the table column 14 and the segments 16, 18, and 20 of the patient support, the operating table may be provided with an adjustment mechanism. For remote control of the adjustment mechanism, the table column 14 may include an infrared transmitting-receiving unit 22.

The infrared transmitting-receiving unit 22 may be adapted to communicate with the pedal switch 50 via infrared signals. For this purpose, the pedal switch may be provided with an infrared transmitting-receiving unit 52 which may be the first infrared transmitting-receiving unit, and a unit 22 provided in the operating table 10 may be the second infrared transmitting-receiving unit.

The pedal switch 50 may include a plurality of operating elements 54, 56, 58, 60, 62, and 64 to be operated by a user by foot in order to remotely control the operating table 10. The operating element 54 may cause the first transmitting-receiving unit 52 to send a control command (e.g., "LIFT UPWARD") to the second infrared transmitting-receiving unit 22. The control command "LIFT UPWARD" may cause upward movement of the table column 14, thereby lifting the patient support as a whole. Correspondingly, the operating element 56 may be assigned to a control command (e.g., "LIFT DOWNWARD") which may lower the patient support.

The operating element 58 may be assigned to a control demand (e.g., "BACK UPWARD") which may cause upward pivoting of a segment 20 of the patient support forming a back panel. Correspondingly, the operating element 60 may be assigned to a control command (e.g., "BACK DOWNWARD") which may cause downward pivoting of the segment 20.

The operating element 62 may be assigned to a control demand (e.g., "LEGS UPWARD"). The control command may cause the operating table to perform upward pivoting of the segment 16 of the patient support forming a leg panel. Correspondingly, the operating element 64 may be assigned to a control command (e.g., "LEGS DOWNWARD") which may cause downward pivoting of segment 16 of the patient support.

Further, the pedal switch 50 may have a motion sensor 66 by which lifting of the pedal switch 50 from the floor or other movement of pedal switch 50 can be detected.

FIG. 1 illustrates a state prior to a start-up of the pedal switch 50 (e.g., in a first exemplary embodiment). In this state, the pedal switch 50 may be brought to the operating room and may be placed on the floor so as to establish a line of sight between the two infrared transmitting-receiving units 52 and 22. In this state there may be no communication between the two infrared transmitting-receiving units 52 and 22.

Figure 2:
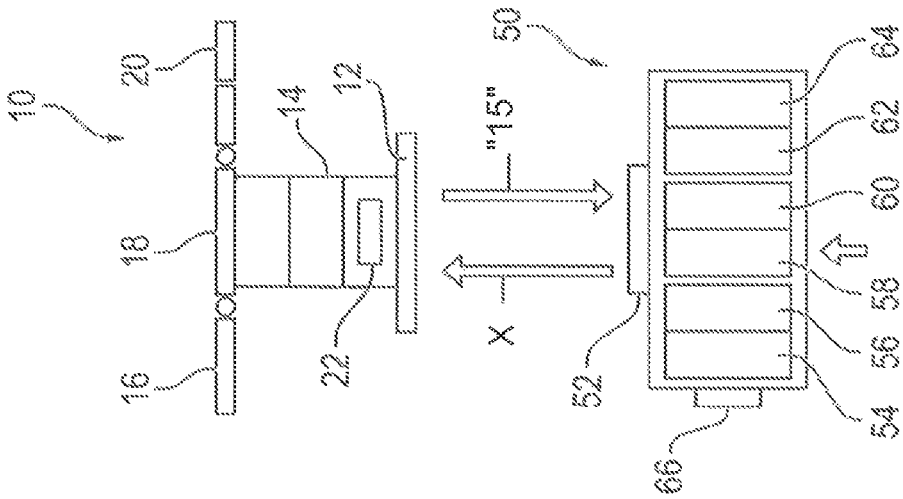
FIG. 2 is a schematic illustration showing the first exemplary embodiment during start-up of the pedal switch.

In FIG. 2, the operator may manipulate the operating element 58 with his/her foot, whereupon the pedal switch 50 may be started. By manipulating the operating element 58, to which the control command "BACK UPWARD" may be assigned, the first infrared transmitting-receiving unit 52 may be caused to send a request command (e.g., request command X) to the second infrared transmitting-receiving unit 22. The request command X may request the second infrared transmitting-receiving unit 22 to send a device address related to the operating table 10 back to the first infrared transmitting-receiving unit 52. Therein, the device address may be individually preset for the operating table 10. For example, the device address may be stored by the operating table 10 and/or the second infrared transmitting-receiving unit 22 (e.g., on a computer-readable medium associated with operating table 10 and/or the second infrared transmitting-receiving unit 22, or, for example, in any other suitable manner for assigning a predetermined device address to operating table 10 and/or the second infrared transmitting-receiving unit 22). Other operating tables (e.g., additional operating tables of a plurality of operating tables) may also have their own device addresses that can be distinguished from other operating table addresses.

As illustrated in FIG. 2, the second infrared transmitting-receiving unit 22 may send the preset device address (e.g., a device address "15"). The device address "15" received by the first infrared transmitting-receiving unit 52 may be adopted as a remote control address in the pedal switch 50. For example, the first infrared transmitting-receiving unit 52 and/or the pedal switch 50 may adopt the device address "15" by recording the device address "15" by any suitable manner (for example, recording the device address "15" received by the first infrared transmitting-receiving unit 52 on a computer-readable medium associated with the first infrared transmitting-receiving unit 52 and/or the pedal switch 50 or by any other manner for assigning the device address "15" to the first infrared transmitting-receiving unit 52 and/or the pedal switch 50). Thus, the device address relating to the operating table and the remote control address relating to the pedal switch 50 may be substantially identical, whereby a paired operating state between the two infrared transmitting-receiving units 52 and 22 may be established.

Figure 3:
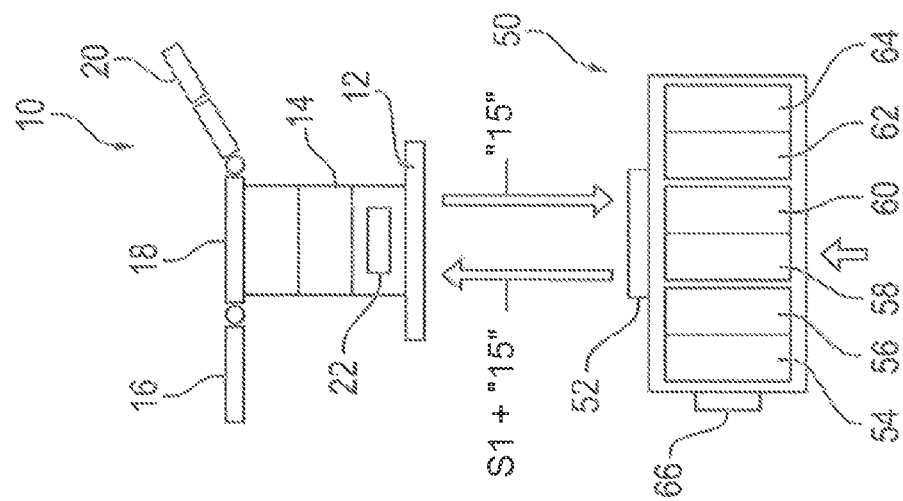
FIG. 3 is a schematic illustration showing the first exemplary embodiment when sending a control command to the operating table.

In the state illustrated in FIG. 3, the operating element 58 may still be manipulated. Thus, the first infrared transmitting-receiving unit 52 may send the control command "BACK UPWARD" assigned to the operating element 58 (e.g., which is designated by S1 in FIG. 3) to the second infrared transmitting-receiving unit 22. Together with the control command S1, the first infrared transmitting-receiving unit 52 may also transmit the infrared address "15" received from the operating table 10 and adopted as a remote control address. The operating table 10 may recognize the paired operating state, e.g., the correspondence between the preset device address and the remote control address received from the pedal switch 50. As the operating table 10 and pedal switch 50 may thus be paired, the adjustment mechanism contained in the operating table 10 may execute the control command "BACK UPWARD" (S1), whereby the segment 20 of the patient support may be pivoted upward.

In the state illustrated in FIG. 3, the second infrared transmitting-receiving unit 22 may cyclically send the device address "15" to the first infrared transmitting-receiving unit 52. Accordingly, it may be verified for the pedal switch 50 whether or not the first infrared transmitting-receiving unit 52 cyclically receives the device address "15". The second infrared transmitting-receiving unit 22 may cyclically send the device address "15" to the first infrared transmitting-receiving unit 52, for example, by sending device address "15" at constant and/or varying intervals (e.g., many times per second, several times per second, about every second, every few seconds, several times per minute, or every few minutes).

In FIG. 4, an operator, starting from the state shown in FIG. 3, may manipulate the operating element 60. Accordingly, the first infrared transmitting-receiving unit 52 may send the control command "BACK DOWNWARD" assigned to the operating element 60, together with the remote control address "15" to the second infrared transmitting-receiving unit 22. For example, this control command may be designated by S2 in FIG. 4. Accordingly, the adjustment mechanism of the operating table 10 may pivot the segment 20 of the patient support downward. As further illustrated in FIG. 4, the second infrared transmitting-receiving unit 22 may continue to cyclically send the device address "15" to the first infrared transmitting-receiving unit 22.

FIG. 5 illustrates a state in which the paired operating state between the two infrared transmitting-receiving units 52 and 22 is cancelled. The state illustrated in FIG. 5 may be caused by the line of sight between the two infrared transmitting-receiving units 52 and 22 no longer being present, and accordingly the first infrared transmitting-receiving unit 52 no longer cyclically receiving the device address. The paired operating state can be terminated by the pedal switch 50 being lifted from the floor or moved from its position and the motion sensor 66 detecting this event. In this case, the motion sensor 66 may output a corresponding signal which may cause termination of the pairing of the two infrared transmitting-receiving units 52 and 22. However, if there is substantially no movement of the pedal switch 50 (e.g., the pedal switch 50 remains substantially stationary), then a paired operating state may be maintained between the two infrared transmitting-receiving units 52 and 22. For example, as there is no pairing in the state illustrated in FIG. 5, the request command X is transmitted again by the first infrared transmitting-receiving unit 52 upon subsequent start-up of the pedal switch 50 (e.g., upon the following manipulation of one of the operating element 54 to 64).

FIGS. 6 to 8 illustrate a second exemplary embodiment of the present disclosure. FIG. 6 illustrates a state that is similar to the state illustrated in FIG. 1. In FIG. 7 the operator may manipulate (e.g., with his/her foot) the operating element 58 to which the control command "BACK UPWARD" may be assigned. As the pedal switch 50 is started by this manipulation, the first infrared transmitting-receiving unit 52 may initially send the request command X by which the operating table 10 (e.g., which has been addressed) is caused to send its own device. In the example illustrated in FIG. 7, this request command is received not only by the operating table 10, but also by the operating table 10' (e.g., which has the same structure as operating table 10 but has a different device address, for example, "25"). Accordingly, the first infrared transmitting-receiving unit receives both the device address "15" and the device address "25". Receipt of two device address based on an operation of the pedal switch 50 may result in no paired operating state at all being established with any one of the operating tables 10 and 10' (e.g., or the paired operating state being terminated if it had already existed). Accordingly, in the state illustrated in FIG. 8, e.g., in which the operating element 58 assigned to the control command "BACK UPWARD" is further manipulated, the pedal switch 50 may not output the control command "BACK UPWARD". Rather, the request command X may continue to be sent.

It will be apparent to those skilled in the art that various modifications and variations can be made to the disclosed method and apparatus. Other embodiments will be apparent to those skilled in the art from consideration of the specification and practice of the disclosed method and apparatus. It is intended that the specification and the disclosed examples be considered as exemplary only, with a true scope being indicated by the following claims.

What is claimed is:

1. An operating table control apparatus, comprising:
a remote control device;
a first transmitting-receiving device that is mountable to the remote control device; and
a second transmitting-receiving device that is mountable to a first operating table;
wherein the first transmitting-receiving device is configured to transmit a request command to the second transmitting-receiving device;
wherein after receiving the request command from the first transmitting-receiving device, the second transmitting-receiving device is configured to transmit a device address of the first operating table to the first transmitting-receiving device;
wherein the first transmitting-receiving device is configured to adopt the device address received from the second transmitting-receiving device, establishing a paired operating state between the first transmitting-receiving device and the second transmitting-receiving device;
wherein the first transmitting-receiving device is configured to transmit both a control command and the device address to the second transmitting-receiving device;
wherein the second transmitting-receiving device is configured to cyclically transmit the device address to the first transmitting-receiving device; and
wherein the first transmitting-receiving device and the second transmitting-receiving device remain in the paired operating state provided that the second transmitting-receiving device cyclically transmits the device address to the first transmitting-receiving device.

2. The operating table control apparatus of claim 1, wherein the first transmitting-receiving device and the second transmitting-receiving device remain in the paired operating state provided that:
a line of sight is maintained between the first transmitting-receiving device and the second transmitting-receiving device;
the remote control device remains substantially stationary; and
a second device address of a second operating table is not received by the first transmitting-receiving device.

3. The operating table control apparatus of claim 1, wherein the first transmitting-receiving device and the second transmitting-receiving device are infrared transmitting-receiving devices.

4. The operating table control apparatus of claim 1, wherein the remote control device is a pedal switch.

5. The operating table control apparatus of claim 1, further comprising a motion sensor that is disposed on the remote control device.

6. The operating table control apparatus of claim 5, wherein the paired operating state between the first transmitting-receiving device and the second transmitting-receiving device is canceled when the motion sensor detects that the remote control device is lifted.

7. The operating table control apparatus of claim 5, wherein the paired operating state between the first transmitting-receiving device and the second transmitting-receiving device is canceled when the motion sensor detects that the remote control device, which is a pedal switch, is lifted from a floor.

8. The operating table control apparatus of claim 1, wherein the device address adopted by the first transmitting-receiving device is stored by the remote control device.

9. A method, comprising:
sending a request command to an operating table infrared device via a remote control infrared device;
receiving a device address from the operating table infrared device via the remote control infrared device;
storing the device address;
establishing a paired operating state between the operating table infrared device and the remote control infrared device based on the device address;
sending both a control command and the device address to the operating table infrared device via the remote control infrared device; and
canceling the paired operating state when a line of sight between the operating table infrared device and the remote control infrared device is blocked, the remote control infrared device is moved, or another device address from another operating table is received by the remote control infrared device.

10. The method of claim 9, further comprising cyclically receiving the device address from the operating table infrared device via the remote control infrared device.

11. The method of claim 9, wherein sending the request command to the operating table infrared device via the remote control infrared device occurs upon a start-up of the remote control infrared device.

12. The method of claim 11, wherein upon a subsequent start-up of the remote control infrared device, the device address stored following the previous start-up is again sent from the remote control infrared device.

13. The method of claim 12, wherein when, upon the subsequent start-up, the device address sent from the remote control infrared device is received by another operating table infrared device having a second device address that is different from the device address sent by the remote control infrared device, a request is output to a user requesting confirmation by the user of the second device address.

14. The method of claim 12, wherein the remote control device is a pedal switch.

15. An operating table system, comprising:
a remote control device;
an operating table;
a first infrared transmitting-receiving device that is mountable to the remote control device; and
a second infrared transmitting-receiving device that is mountable to the operating table;
wherein the first infrared transmitting-receiving device is configured to transmit a request command to the second infrared transmitting-receiving device;
wherein after receiving the request command from the first infrared transmitting-receiving device, the second infrared transmitting-receiving device is configured to transmit a device address of the operating table to the first infrared transmitting-receiving device;
wherein the first infrared transmitting-receiving device is configured to adopt the device address received from the second infrared transmitting-receiving device, establishing a paired operating state between the first infrared transmitting-receiving device and the second infrared transmitting-receiving device;
wherein the first infrared transmitting-receiving device is configured to transmit both a control command and the device address to the second infrared transmitting-receiving device; and
wherein the first infrared transmitting-receiving device and the second infrared transmitting-receiving device remain in the paired operating state provided that a line of sight is maintained between the first infrared transmitting-receiving device and the second infrared transmitting-receiving device, and the remote control device remains substantially stationary.

16. The operating table system of claim 15, wherein the paired operating state between the first infrared transmitting-receiving device and the second infrared transmitting-receiving device is canceled when a second device address is received by the first infrared transmitting-receiving device from another operating table.

17. The operating table system of claim 15, wherein the device address is cyclically received by the first infrared transmitting-receiving device from the second infrared transmitting-receiving device.

18. The operating table system of claim 15, wherein the remote control device is a pedal switch.

19. The operating table system of claim 15, further comprising a motion sensor that is disposed on the remote control device.

20. The operating table system of claim 19, wherein the paired operating state between the first infrared transmitting-receiving device and the second infrared transmitting-receiving device is canceled when the motion sensor detects that the remote control device, which is a pedal switch, is lifted from a floor.

* * * * *